US010472300B2

(12) United States Patent
Minoux et al.

(10) Patent No.: US 10,472,300 B2
(45) Date of Patent: Nov. 12, 2019

(54) PROCESS FOR PREPARING OLEFINS BY DEHYDRATING ALCOHOLS WITH LESS SIDE EFFECTS COMPRISING ADDITION OF SULFUR CONTAINING COMPOUNDS

(71) Applicants: Total Research & Technology Feluy, Seneffe (Feluy) (BE); IFP Energies Nouvelles, Rueil Malmaison (FR)

(72) Inventors: Delphine Minoux, Nivelles (BE); Nikolai Nesterenko, Nivelles (BE); Cindy Adam, Wierde (BE); Walter Vermeiren, Houthalen (BE); Philip De Smedt, Sint-Niklaas (BE); Jean-Pierre Dath, Beloeil (BE); Vincent Coupard, Villeurbanne (FR); Sylvie Maury, Saint Maurice d'Argoire (FR); Nicolas Aribert, Moirans (FR)

(73) Assignees: Total Research & Technology Feluy, Seneffe (BE); IFP Energies Nouvelles, Rueil Malmaison (FR)

( * ) Notice: Subject to any disclaimer, the term of this patent is extended or adjusted under 35 U.S.C. 154(b) by 0 days.

(21) Appl. No.: 15/540,327

(22) PCT Filed: Dec. 18, 2015

(86) PCT No.: PCT/EP2015/080437
§ 371 (c)(1),
(2) Date: Jun. 28, 2017

(87) PCT Pub. No.: WO2016/107759
PCT Pub. Date: Jul. 7, 2016

(65) Prior Publication Data
US 2017/0355650 A1    Dec. 14, 2017

(30) Foreign Application Priority Data
Dec. 31, 2014  (EP) .................................. 14290404

(51) Int. Cl.
*C07C 1/24*      (2006.01)
*B01J 37/28*     (2006.01)
*B01J 29/06*     (2006.01)
*B01J 29/40*     (2006.01)

(52) U.S. Cl.
CPC ................. *C07C 1/24* (2013.01); *B01J 29/06* (2013.01); *B01J 29/40* (2013.01); *B01J 37/28* (2013.01); *B01J 2229/123* (2013.01); *B01J 2229/20* (2013.01); *B01J 2229/34* (2013.01); *B01J 2229/36* (2013.01); *B01J 2229/37* (2013.01); *B01J 2229/42* (2013.01); *C07C 2521/04* (2013.01); *C07C 2521/06* (2013.01); *C07C 2521/12* (2013.01); *C07C 2529/40* (2013.01); *C07C 2529/65* (2013.01); *C07C 2529/85* (2013.01); *Y02P 20/52* (2015.11)

(58) Field of Classification Search
CPC ..................................................... C07C 1/24
See application file for complete search history.

(56) References Cited

U.S. PATENT DOCUMENTS

| 3,911,041 | A  |   | 10/1975 | Kaeding et al. |
| 4,232,179 | A  |   | 11/1980 | Valladares et al. |
| 4,396,789 | A  |   | 8/1983 | Barrocas et al. |
| 4,847,223 | A  |   | 7/1989 | Le Van Mao et al. |
| 5,573,990 | A  |   | 11/1996 | Wang et al. |
| 6,797,851 | B2 |   | 9/2004 | Martens et al. |
| 9,249,066 | B2 | * | 2/2016 | Minoux .................... C07C 1/24 |
| 2008/0261230 | A1 |   | 10/2008 | Liao et al. |
| 2010/0197485 | A1 |   | 8/2010 | Johnston et al. |

(Continued)

FOREIGN PATENT DOCUMENTS

| CN | 101244971 A | 8/2008 |
| EP | 2151423 A1 | 2/2010 |

(Continued)

OTHER PUBLICATIONS

International Search Report issued in PCT/EP2015/080437, dated Mar. 8, 2016, 4 pages.

*Primary Examiner* — Philip Y Louie
*Assistant Examiner* — Alyssa L Cepluch
(74) *Attorney, Agent, or Firm* — Albert Shung

(57) ABSTRACT

The present invention is a process for dehydrating an alcohol to prepare a corresponding olefin, comprising:
(a) providing a composition (A) comprising at least an alcohol having at least 2 carbon atoms, optionally water, optionally an inert component, in a dehydration unit,
(b) placing the composition (A) into contact with an acidic catalyst in a reaction zone of said dehydration unit at conditions effective to dehydrate at least a portion of the alcohol to make a corresponding olefin,
(c) recovering from said dehydration unit an effluent (B) comprising:
at least an olefin,
water,
undesired by-products including aldehydes and light products,
optionally unconverted alcohol(s),
optionally the inert component,
wherein,
said composition (A)—providing step (a) comprises adding an effective amount of one or more sulfur containing compound capable to reduce the undesired by-products by comparison with a non introduction of such sulfur containing compound.
The component introduced at step (a) can be chosen from the group consisting of thiols, sulfides, disulfides.

19 Claims, No Drawings

(56) References Cited

U.S. PATENT DOCUMENTS

| | | | |
|---|---|---|---|
| 2011/0124939 A1* | 5/2011 | Minoux | C07C 1/24 585/639 |
| 2011/0196113 A1* | 8/2011 | Nesterenko | B01J 21/08 526/75 |
| 2012/0059139 A1* | 3/2012 | Hayashi | B01J 29/70 526/351 |
| 2013/0131399 A1* | 5/2013 | Weiner | B01J 37/0205 568/885 |
| 2013/0158301 A1* | 6/2013 | Wollrab | C07C 29/149 568/885 |
| 2013/0217943 A1* | 8/2013 | Minoux | C07C 1/24 585/640 |
| 2015/0152024 A1* | 6/2015 | Iitsuka | B01J 8/1809 585/412 |
| 2016/0194257 A1* | 7/2016 | Lilga | B01J 23/755 585/255 |

FOREIGN PATENT DOCUMENTS

| | | | |
|---|---|---|---|
| WO | 2009016153 A1 | 2/2009 | |
| WO | 2009092779 A2 | 7/2009 | |
| WO | 2009092781 A2 | 7/2009 | |
| WO | 2011002699 A2 | 1/2011 | |
| WO | 2009098262 A1 | 7/2011 | |
| WO | 2011089262 A1 | 7/2011 | |
| WO | 2011161045 A1 | 12/2011 | |
| WO | 2013017496 A1 | 2/2013 | |
| WO | 2013017497 A1 | 2/2013 | |
| WO | 2013017498 A1 | 2/2013 | |
| WO | WO-2014025021 A1 * | 2/2014 | B01J 8/1809 |

* cited by examiner

PROCESS FOR PREPARING OLEFINS BY DEHYDRATING ALCOHOLS WITH LESS SIDE EFFECTS COMPRISING ADDITION OF SULFUR CONTAINING COMPOUNDS

CROSS-REFERENCE TO RELATED APPLICATIONS

This application claims the benefit of PCT/EP2015/080437 filed Dec. 18, 2015, which claims priority from EP 14290404.4 filed Dec. 31, 2014, which are incorporated herein by reference in their entireties for all purposes.

FIELD OF THE INVENTION

The present invention relates to dehydration of alcohols to make olefins, in particular to prepare the corresponding olefin, with reduced side reactions, in other words with reduced amount of by-products. "Corresponding olefins" means an olefin having the same number of carbon atoms as the alcohol precursor.

The present invention relates to a method for the dehydration of substantially one single alcohol or a mixture of alcohols characterised by an increased yield for the corresponding olefin with the same number of carbon atoms by lowering the formation of undesired by-products, in particular aldehyde(s) and light products ($H_2$, CO, $CO_2$, $CH_4$), using appropriate spiking of the alcohol feed with a sulfur containing compound.

The invention can be used for a dehydration unit comprising any type of reactors (batch, moving, fixed or fluidized bed), the reactors operating either under adiabatic or isothermal conditions. The invention is particularly useful for dehydration units comprising fixed, moving or fluidized bed reactors.

BACKGROUND OF THE INVENTION

Alcohol dehydration reactions to produce alkenes have been known for a long time. Usually these reactions are performed in presence of solid acid catalysts, the conversion of alcohol being nearly complete. However, in view of the potential downstream applications of olefins, it is of particular importance to limit the amounts of secondary products to gain in process efficiency and to save expensive downstream steps of separation/purification.

It has been observed, in addition to dehydration of alcohol to the corresponding olefin, formation of aldehyde, in particular formation of the corresponding aldehyde, and formation of light products such as $H_2$, CO, $CO_2$ and $CH_4$). It is supposed that formation of $H_2$ and CO results mainly from degradation of said aldehydes under the conditions of the dehydration reactions. Formation of $CO_2$, $H_2$ and $CH_4$ may result from other kind of side reactions. For example, during dehydration of ethanol, formation of acetaldehyde, $CH_4$, $H_2$, CO, $CO_2$ is observed.

Similar undesirable secondary by-products can be observed during dehydration of other alcohols. These secondary products lead to lower once-through yield of the corresponding olefin and important losses of the olefin, in particular in downstream purification section. The formation of these products is still not well understood and solutions provided by prior art to reduce the formation of these secondary products are limited.

WO2011/002699 discloses a process for producing olefins by dehydration of alcohols in reactors under either adiabatic or isothermal conditions. The process comprises reacting under first reaction conditions an aliphatic alcohol, optionally diluted with water, in the presence of a dehydration catalyst to form a first reaction product that includes dialkyl ether and generated water, and further reacting under second reaction conditions the first reaction product in the presence of a dehydration catalyst to form olefin by dehydration of the dialkyl ether. The temperature of the second reaction conditions is at least 10° C. higher than the temperature of the first reaction conditions. In particular, the temperature of the first reaction conditions ranges from 200° C. to 450° C., while the temperature of the second reaction conditions ranges from 250° C. to 500° C., preferably from 400° C. to 450° C. The purpose of the relatively low temperature range in the first reactor is to instigate reaction of the aliphatic alcohol to primarily its corresponding dialkyl ether, which dehydration serves to increase the water content of the first reaction product. The effect of the temperature increase between the first and second reactors is that the amount of dialkyl ether may be progressively reduced as dehydration is carried to or toward completion, to form the final desired olefin, and the reduction in starting diluent water with the alcohol feed means that there is a minimum of corresponding aldehyde formed. There is no mention of other by-products such as $H_2$, CO, $CO_2$ & $CH_4$.

U.S. Pat. No. 4,232,179 relates to a process for preparing ethene by dehydrating ethyl alcohol in the presence of catalysts using adiabatic reactors at high temperature. In that process, the necessary heat to maintain the temperature of the catalyst bed at levels compatible with the desired conversion is supplied by the simultaneous introduction of the feed and a sensible heat carrying fluid, which may be selected from, for example, a part of the effluent from the reactor used as a recycle stream, steam supplied by an external source, other adequate fluids for the process, or any combination thereof. The use of diluted ethyl alcohol in the sensible heat carrying fluid stream leads to considerable reduction in the formation of C3 and C4 by-products, as well as in the deposition of coke over the catalyst, these peculiar features leading to highly pure ethene. There is no mention of other by-products such as $H_2$, CO, $CO_2$ or $CH_4$.

U.S. Pat. No. 4,396,789 relates to a process for the dehydration of ethanol to form ethene in fixed adiabatic reactors containing a dehydration catalyst. The process includes the recycling of unreacted ethanol to the process, feeding the charge to the initial reactor at a pressure of 20 to 40 atm, withdrawing the ethane from the final reactor at a pressure of no less than 18 atm, and passing at least a portion of said reaction effluent to cryogenic purification with further compression. Ethyl alcohol is introduced with steam at a temperature from 400° C. to 520° C. and a pressure from 20 to 40 atm. Subsequent washing and purification steps permit to obtain a high purity ethene. There is no mention of by-products such as $H_2$, CO, $CO_2$ & $CH_4$.

WO2011/161045 relates to the dehydration of alcohols on acidic catalysts to make the corresponding olefins. The unselective reactions that need to be suppressed are (i) altering in number of carbon atoms compared to the alcohol through oligomerisation and cracking reactions and (ii) the formation of paraffins and aromatics or coke through hydrogen-transfer reactions. In that process, the activity and selectivity of alcohol dehydration catalyst is adjusted by poisoining the unselective acid sites of the catalyst by spiking the feed with a neutralizing agent while keeping active the selective acidic sites of the catalyst. The neutralizing agent can be chosen from basic compounds: ammonia, organic ammonium salts, hydrazine, nitriles, amines, (including pyridines, pyrrols, pyrrolydones and pyrrolidines), amides, imines, di-imines, imides, cyanates, isocyanates, nitrites and nitroso compounds. aldehydes, ketones, carboxylic esters, and their corresponding thio-compounds (thiols, sulphides, disulfides). Secondary light products as $H_2$, CO, $CO_2$, $CH_4$ are not mentioned. The spiking is used to moderate the excess of catalyst acidity.

WO2010/012564 corresponding to EP 2 151 423 relates to a process to make olefins from oxygenates with reduced side reactions wherein reactor walls are pre-treated by injection of sulphur containing compounds. The conversion of said oxygenates is referred as MTO process in which methanol is converted to $C_2$ to $C_4$ olefins. It has nothing to see with the present invention which relates to the dehydration of alcohols on acidic catalysts to make the corresponding olefins. In particular the formation of the by-products occurs via different reaction mechanism and side reactions of the MTO process are different from the side reactions of the alcohols dehydration reactions.

U.S. Pat. No. 4,847,223 discloses the deposition of trifluoromethanesulfonic acid (TFA) onto an acid-form pentasil zeolite to convert ethanol into ethylene. Such acid is coated on the catalyst, HZSM-5 being exemplified. The TFA stays on the catalyst and is not part of the stream of ethanol to be dehydrated.

WO 2013/017496 discloses the dehydration of ethanol over a P-ZSM-5 catalyst. This application discloses a particular catalyst composition tested for the dehydration of the ethanol. However this application is not concerned about the amount of H2, CO, CH4 produced by the catalyst and the way to limit the formation of such by-products.

Prior arts teach us how to improve selectivity in the dehydration products by poisoning the unselective acid sites on the catalyst and inhibit cracking and oligomerization of the alkenes. However, formation of $H_2$, CO, $CO_2$, $CH_4$ by-products typically occurs via a different route relative to the acid catalyzed reaction pathway. So, an object of the present invention is to reduce formation of secondary by-products, in particular formation of aldehydes and of light products such as $H_2$, CO, $CO_2$ & $CH_4$.

A convenient solution has been discovered to reduce the amount of secondary products, light products ($H_2$, CO, $CO_2$ & $CH_4$) and aldehydes, and to improve the yield of olefin in alcohol dehydration reactions by adding sulfur containing compounds with the alcohol feed.

Without willing to be bound by any theory, it is supposed that metallic sites, which are able to promote the formation of the aldehyde, in particular the corresponding aldehyde, may catalyze side reactions leading to the formation of these secondary by-products. In particular, it is believed that a transformation of the alcohol into the corresponding aldehyde first occurs and is followed by formation of light products such as $H_2$, CO, by degradation of this corresponding aldehyde into lighter products, for example by decarbonylation of the aldehyde. Formation of $CH_4$, $CO_2$, but also of some $H_2$, may result from other side reactions, probably catalyzed by the same sites.

The origin of these metallic sites is still uncertain and may be various. They are thought to be present on metallic internal surface of the dehydration unit, in particular metallic internal surface in contact with the feed before the entry of the feed in the reaction zone or in the reaction zone. It is also thought that the sites may also be present on catalyst, either as part of the catalyst or coming from degradation by corrosion of these metallic internal surfaces in contact with the feed. It is also believed that regeneration of the catalyst may lead to an activation of the sites responsible for the formation of the above mentioned undesirable by-products.

Without willing to be bound by any theory, it is supposed that sulfur containing compounds poison, probably via a preferential adsorption mechanism, the sites on which these secondary products are formed. It seems that sulfur containing compounds can selectively poisons the most active sites, which dramatically reduces side reactions and improves the yield of olefin.

BRIEF SUMMARY OF THE INVENTION

An object of the present invention is a process for dehydrating an alcohol to prepare corresponding olefin(s), comprising:

(a) providing a feed (A) comprising at least an alcohol having at least 2 carbon atoms, and preferably at most 5 carbon atoms, or a mixture thereof optionally water, optionally an inert component, in a dehydration unit, (b) placing the feed (A) into contact with an acidic catalyst in a reaction zone of said dehydration unit containing metallic sites at conditions effective to dehydrate at least a portion of the alcohol to make an olefin or a mixture of olefins having the same number of carbon atoms as the alcohol, (c) recovering from said dehydration unit an effluent (B) comprising:
an olefin or a mixture of olefins,
water,
undesired by-products including aldehydes, in particular the corresponding aldhehydes, and light products, comprising $H_2$, CO, $CO_2$, $CH_4$,
optionally unconverted alcohol(s) if any,
optionally the inert component,
wherein,
said feed (A)—providing step (a) being further characterized in that an effective amount of one or more sulphur containing compound capable to reduce the undesired by-products produced by the reforming secondary reaction of said alcohol over said metallic sites by comparison with a non introduction of such sulphur containing compound is added to said feed (A) at step (a) at a sulphur weight concentration of at least 0.5 wt ppm preferably at least 1 wt ppm more preferably at least 2 wt ppm and at most 20 wt ppm preferably at most 10 wt ppm and more preferably at most 5 wt ppm of the total content of said feed (A) with said sulphur containing compound. The invention is further remarkable in that said acidic catalyst is at least one compound selected from the group consisting of:
A crystalline silicate zeolite having a ratio Si/Al higher than 10,
A dealuminated crystalline silicate zeolite,
A phosphorous modified zeolite,
silica-alumina,
alumina,
silicated, titanated, zirconated or fluorinated alumina
silico-aluminophosphates,
or a modified crystalline aluminosilicate of the Framework Type FER having Si/Al framework molar ratio greater than 20 and a ratio between strong acid sites and weak acid sites, S/W, lower than 1.0, the ratio S/W being measured by temperature-programmed desorption of ammonia and being determined by the ratio of the peak area of ammonia desorbed above 340° C. to that desorbed below 340° C.,
or any of above cited acidic catalyst, which was subjected to a preliminary pre-coking step.

As a result of said addition of sulphur containing compound, the formation of undesired by-products is reduced and yield for the desired corresponding olefin is increased.

It has been additionally discovered that sulphur containing compound should be added at a relatively low concentration in stream (A) in order to deactivate preferentially the metallic sites before the acidic catalyst sites. Indeed under the operating condition of the dehydration of alcohol, a too high concentration of sulphur containing compound (higher than 20 wt ppm) would lead to catalyst deactivation instead of increase of selectivity. On the contrary to the MTO reaction, the need for sulphur containing compound is less important for a dehydration reaction mainly because the operating temperature is lower. The typical operating temperature for MTO is of at least 550° C. whereas the typical temperature for alcohol dehydration is in the range of 300 to 450° C. The impact of sulphur containing compound varies drastically with the temperature: under the MTO reaction temperature i.e. at a relatively high temperature, sulphur containing compound have only little effect on the acidity of the catalyst and therefore on the catalyst conversion. On the contrary, under the dehydration reaction temperature i.e. at a relatively lower temperature, sulphur containing compound can have a significant impact on the catalyst acidity and therefore on its conversion. It is therefore necessary to finely tune the sulphur containing compound concentration in stream (A).

The present invention is particularly useful for dehydrating units presenting at least one metallic internal wall, in particular containing iron such as steel. Said metallic internal wall may be part of a reactor, pipe or any other equipment of the dehydrating unit in contact with feed (A).

With regards to said effluent (B) of the dehydration unit, the corresponding aldehyde means aldehydes resulting from the transformation of an alcohol contained in the feed (A) with the same number of carbon atoms. The light products are mainly $H_2$, CO, $CO_2$, $CH_4$. Some light products result from degradation of aldehydes, such as alkenes of lower number of carbon atoms than the aldehyde, or gaseous compounds such as $H_2$, CO.

In another specific embodiment, said effective amount of one or more sulphur containing compound capable to reduce the undesired by-products by comparison with a non introduction of such compound is determined with the following steps:
  performing said dehydration of step (b) without introducing said sulphur containing compound chosen among organic acids in stream (A)
  measuring said content of undesired by-products including aldehydes and light products, in particular $H_2$, CO, $CH_4$, in said effluent (B) obtained at step (b)
  increasing the content of said sulphur containing compound by increments of 0.5 wt ppm until the total content of undesired by-products including aldehydes and light products, in particular $H_2$, CO, $CH_4$, in said effluent (B) obtained at step (b) is lower than 4 wt %.

In a specific embodiment, said feed (A)—providing step comprises adding one or more sulfur-containing compound(s) to the feed (A) or directly in the dehydration unit.

According to a specific embodiment:
  the recovery step (c) comprises recovering unconverted alcohol(s), said process further comprising, subsequent to recovery step (c), a step of:
  (d) recycling the unconverted alcohol to said feed (A)—providing step (a), in the dehydration unit.

In another embodiment, said step (d) of recycling the unconverted alcohol to said feed (A)—providing step (a) contains the sulphur containing compound, at the inlet of the dehydration. It has been particularly discovered that part of sulphur containing compound can be found in said unconverted alcohols. Such mixture of unconverted alcohols and of sulphur containing compound can be recycled at the inlet of the dehydration unit. By doing it is possible to reduce the amount of sulphur containing compound capable to reduce the undesired by-products by comparison with a non introduction of such sulphur containing compound added to said feed (A) at step (a) while still maintaining the production of un-desired by-products at the exit of said dehydration unit at the level obtained without said recycling. In other word, the addition of fresh sulphur containing compound (i.e. sulphur containing compound that does not exit from the dehydration unit) before being introduced feed (A) at step (a) is limited so that the overall of sulphur containing compound (fresh and recycled) content in said feed (A) entering the dehydration unit is at the same level as if there was not recycling. It has also been discovered that a relative equilibrium for the production of un-desired by product including sulphur containing compound is quickly reached when said unconverted alcohol is recycled. During the start up of the unit, a large quantity of "fresh" sulphur containing compound should be added at the inlet of the dehydration unit, then the equilibrium is reached and the "fresh" sulphur containing compound introduced shall be reduced as some sulphur containing compound are recycled.

According to a specific embodiment, the recovering step (c) may comprise recovering the olefin(s) and the unconverted alcohol(s), as well as each compound contained in the effluent (B), by means of fractionating.

In an embodiment the acidic catalyst is at least one compound selected from the group consisting of:
A crystalline silicate zeolite having a ratio Si/Al higher than 10,
A dealuminated crystalline silicate zeolite,
A phosphorous modified zeolite,
silica-alumina,
alumina,
silicated, titanated, zirconated or fluorinated alumina
silico-aluminophosphates,
a modified crystalline aluminosilicate of the Framework Type FER having Si/Al framework molar ratio greater than 20 and a ratio between strong acid sites and weak acid sites, S/W, lower than 1.0, the ratio S/W being measured by temperature-programmed desorption of ammonia and being determined by the ratio of the peak area of ammonia desorbed above 340° C. to that desorbed below 340° C.,
or any of above cited acidic catalyst, which was subjected to a preliminary pre-coking step.

In a specific embodiment, said olefin(s) recovered in step c) may be used for production of polymers and elastomers, in particular after appropriated purification and transformation. In another specific embodiment, said olefin(s) recovered in step c) may be used form production of fuel, in particular after appropriated purification and transformation. In another embodiment, the process according the invention is also further remarkable in that said sulphur containing compound is able to passivated at least a part of the inner surface of said dehydration unit such that there is a reduction of the undesired by-products produced by the reforming secondary reaction of said alcohol over said metallic sites by comparison with a non introduction of such sulphur containing compound wherein said passivation is performed prior to step (a) or (b).

DETAILED DESCRIPTION OF THE INVENTION

As regards the feed provided at step (a), the alcohol is any alcohol provided it can be dehydrated to the corresponding olefin, having a same number of carbon atoms. By way of example mention may be made of alcohols having from at least 2 to 5 carbon atoms, preferably from at least 2 to 4 carbon atoms. Advantageously, the invention is of particular interest for ethanol, propanol, butanol (iso, n and tertio).

The feed provided at step (a) can be a mixture of the above alcohols in any proportions, in particular a mixture of ethanol and propanol. The alcohols contained in the mixture may have the same number of carbon atoms or different number of carbon atoms.

Preferably, the alcohol may be ethanol, propanol, isopropanol, 1-butanol, 2-butanol, isobutanol, pentan-1-ol, 3-Methylbutan-1-ol, 2-Methylbutan-1-ol, 2,2-Dimethylpropan-1-ol, pentan-3-ol, Pentan-2-ol, 3-Methylbutan-2-ol, 2-Methylbutan-2-ol, or mixture thereof.

Preferably, the alcohol(s) is (are) provided from biomass fermentation or biomass gasification to syngas, optionally followed by a modified Fischer-Tropsch synthesis. As such, the alcohol(s) may contain impurities such as sulfur containing compounds in a content of less than 0.5 wppm related to the alcohol(s).

For example, the alcohol(s) may be bio-alcohol(s) issued from edible or non-edible biomass. Such bio-alcohols may be obtained by any existing route, for example via hydrogenation of corresponding aldehydes, ketones or acids issued from edible or non-edible biomass.

The alcohol(s) may also be obtained via syn-gas route or synthesized via partial oxidation of paraffin.

Alcohols, in particular ethanol, thus far are the only renewable liquid fuel produced in commercial quantities primarily by the fermentation of sugars for use as a blending component in gasoline.

Most of the world's ethanol is produced by fermentation, using edible biomass such as crops in particular sugar cane, sugar beet, corn, rice and maize. Municipal waste (non edible biomass) can also be used as feedstock, reducing landfill disposal and turning rubbish into a valuable product. For instance, such a process might proceed by the conversion of sucrose by the enzyme invertase into glucose and fructose, then the conversion of glucose by the enzyme zymase into ethanol (and carbon dioxide).

Recently, new biochemical routes have been developed to produce selectively isobutanol from carbohydrates. The new strategy uses the highly active amino acid biosynthetic pathway of microorganisms and diverts its 2-keto acid intermediates for alcohol synthesis. 2-Keto acids are intermediates in amino acid biosynthesis pathways. These metabolites can be converted to aldehydes by 2-keto-acid decarboxylases (KDCs) and then to alcohols by alcohol dehydrogenases (ADHs). Two non-native steps are required to produce alcohols by shunting intermediates from amino acid biosynthesis pathways to alcohol production (US patent 2008/0261230). Recombinant microorganisms may be required to enhance the flux of carbon towards the synthesis of 2-keto-acids. For example, in the valine biosynthesis 2-ketoisovalerate is an intermediate. Glycolyse of carbohydrates results in pyruvate that is converted into acetolactate by acetolactate synthase. 2,4-dihydroxyisovalerate is formed out of acetolactate, catalysed by isomeroreductase. A dehydratase converts the 2,4-dihydroxyisovalerate into 2-keto-isovalerate. In the next step, a keto acid decarboxylase makes isobutyraldehyde from 2-keto-isovalerate. The last step is the hydrogenation of isobutyraldehyde by a dehydrogenase into isobutanol.

Non-edible biomass, like cellulosic materials are both sustainable and available in large quantities.

Strategy of the alcohols production from non-edible biomass, including cellulosic biomass such as wood chips, corn stover, corn cobs and municipal solid waste, is based either on biochemical approaches or on a thermochemical approach.

Three core biochemical conversion technologies enable the conversion of biomass into ethanol: (a) pretreatment (including prehydrolysis), (b) saccharification or hydrolysis and (c) fermentation. Pretreatment involves milling and exposure to chemicals and heat to reduce the size of the plant fibers and hydrolyze a portion of the material to yield fermentable C5 sugars. Saccharification utilizes enzymes to hydrolyze another portion to C6 sugar. Bioengineered microorganisms ferment the various sugars to chemical products in fermentation.

Recent advances in biotechnology have led to the development of the microorganisms to produce ethanol via fermentation from the five sugars in cellulose (arabinose, galactose, glucose, mannose and xylose).

The thermochemical approach considers gasification of biomass or bio-methane to syngas followed by chemical synthesis of ethanol or heavy alcohols over heterogeneous catalyst from syngas.

The syngas could be also converted via microbial fermentation to ethanol. The technology is commercial and is offering by several companies. Coskata claims to have proprietary microorganisms that can convert syngas into useful chemicals or fuels, and LanzaTech has been operating a pilot plant in New Zealand.

Another option is to converts syngas, to methanol which is reacted with CO to produce acetic acid. The acetic acid could be further converted to ethanol by hydrogenation. The hydrogenation step would be conducted in the vapor phase using, for example a Pt—Sn catalyst (US 2010/0197485).

The inert component optionally provided in step (a) is any component provided there is no adverse effect on the catalyst. Because the dehydration is endothermic the inert component can be used to bring energy. By way of examples the inert component is selected among the saturated hydrocarbons having up to 10 carbon atoms, naphtenes, nitrogen. An example of inert component can be any individual saturated compound, a synthetic mixture of the individual saturated compounds as well as some equilibrated refinery streams like straight naphtha, butanes etc. Advantageously it is a saturated hydrocarbon or a mixture of saturated hydrocarbons having from 3 to 7 carbon atoms, more advantageously having from 4 to 6 carbon atoms and is preferably pentane.

The weight proportions of respectively alcohols, water and inert component are, for example, 5-100/0-95/0-95 (the total being 100). The feed (A) can be liquid or gaseous. Depending on the type of the reaction zone (in batch or continuously), the feed (A) may be provided as a flowing stream.

As regards the reaction zone of the dehydration unit, it can comprise one or several reactors in series or in parallel. Reactor(s) may be a batch reactor, fixed bed reactor (radial, isothermal, adiabatic etc), a moving bed reactor or a fluidized bed reactor. A typical fluid bed reactor is one of the FCC type used for fluidized-bed catalytic cracking in the oil refinery. A typical moving bed reactor is of the continuous catalytic reforming type.

The dehydration reactions may be performed continuously in a fixed bed reactor configuration using several reactors in series of equal or different sizes or a pair of parallel "swing" reactors. The various preferred catalysts of the present invention have been found to exhibit high stability. This enables the dehydration process to be performed continuously in two parallel "swing" reactors wherein when one reactor is operating, the other reactor is undergoing catalyst regeneration. The catalyst used in the present invention also can be regenerated several times.

The invention is particularly adapted to moving or fluidized bed reactors. In such reactors, the moving particles of catalyst have an abrasive effect on the reactor wall avoiding the deposition of any coating. The internal surface of the reactor thus remains clean, which may favour the formation of secondary reactions. Addition of the sulfur containing compound(s) during the process permits to reduce these secondary reactions.

The dehydration unit may further comprise one or more other zones such as a heating zone for heating the feed before its entry into in the reaction zone, a separation zone for separating the effluent exiting the reaction zone and recovering the different products obtained, a purification zone for purification of the olefin(s) produced.

As regards the pressure in step (b), the pressure of the reaction zone in the dehydration unit step b) can be any pressure but it is more economical to operate at moderate pressure. By way of example the pressure of the reaction zone ranges from 0.5 to 30 bars absolute (50 kPa to 3 MPa), advantageously from 0.5 to 20 bars absolute (50 kPa to 2 MPa), advantageously from 1 to 20 bars absolute (0.1 MPa to 2 MPa), more advantageously from 1 to 17 bars absolute (0.1 MPa to 1.7 MPa). Advantageously, the partial pressure of the alcohols is advantageously lower than 10 bars absolute (1 MPa) and more advantageously from 0.1 to 4 bars absolute (0.01 MPa to 0.4 MPa), preferably lower than 3.5 bars absolute (0.35 MPa) and more preferably lower than 3 bars absolute (0.3 MPa).

As regards the temperature of the reaction zone in the dehydration unit, it ranges advantageously from 220° C. to 500° C., advantageously from 250° C. to 500° C., more advantageously from 280° C. to 500° C. and preferably from 300° C. to 450° C.

In a reaction zone operating in adiabatic mode, these temperatures refer substantially to the temperature of the alcohol feed entering into the reaction zone. For example, the feed enters at a temperature from 300° C. to 500° C. and exits the reactor at a temperature from 220 to 450° C.

In a reactor operating in isothermal mode, these temperatures refer substantially to the average catalyst bed temperature and can range from 220 to 450° C.

The ethanol dehydration is an endothermic reaction and requires the input of reaction heat in order to maintain catalyst activity sufficiently high and shift the thermodynamic equilibrium to sufficiently high conversion levels.

In case of fluidised bed reactors: (i) for stationary fluidised beds without catalyst circulation, the average catalyst bed temperature is substantially homogeneous throughout the catalyst bed; (ii) in case of circulating fluidised beds where catalyst circulates between a converting reaction section and a catalyst regeneration section, depending on the degree of catalyst backmixing the temperature in the catalyst bed approaches homogeneous conditions (a lot of backmixing) or approaches plug flow conditions (nearly no backmixing) and hence a decreasing temperature profile will install as the conversion proceeds.

In case of fixed bed or moving bed reactors, a decreasing temperature profile will install as the conversion of the alcohol proceeds. In order to compensate for temperature drop and consequently decreasing catalyst activity or approach to thermodynamic equilibrium, reaction heat can be introduced by using several catalyst beds in series with interheating of the reactor effluent from the first bed to higher temperatures and introducing the heated effluent in a second catalyst bed, etc. When fixed bed reactors are used, a multi-tubular reactor can be used where the catalyst is loaded in small-diameter tubes that are installed in a reactor shell. At the shell side, a heating medium is introduced that provides the required reaction heat by heat-transfer through the wall of the reactor tubes to the catalyst.

As regards the WHSV of the composition (A), it ranges advantageously from 0.1 to 30 $h^{-1}$, advantageously from 1 to 25 $h^{-1}$, more advantageously from 3 to 25 $h^{-1}$, more preferably from 4 to 25 $h^{-1}$.

As regards the effluent (B), it comprises essentially water, olefin(s), the inert component (if any) and unconverted alcohol(s). Said unconverted alcohol(s) is supposed to be as less as possible. The olefin(s) is (are) recovered by usual fractionation means. Advantageously the inert component, if any, is recycled in the feed (A)—providing step (a) as well as unconverted alcohol(s), if any. Optionally, a part of the water is recovered by fractionation and recycled to the dehydration unit in step (a).

As regards the dehydration catalyst of step (b), it can be any acid catalyst capable to cause the dehydration of alcohols under above said conditions. One can cite molecular sieves, zeolites, modified zeolites (including P-modified zeolites) silica-alumina, alumina, silicated, titanated, zirconated or fluorinated alumina, silico-aluminophosphates, as well as modified crystalline aluminosilicate of the Framework Type FER having Si/Al framework molar ratio greater than 20 and a ratio between strong acid sites and weak acid sites, S/W, lower than 1.0.

According to an embodiment the catalyst is a crystalline silicate containing advantageously at least one 10 members ring into the structure. It is by way of example of the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), EUO (ZSM-50, EU-1), MFS (ZSM-57) and ZSM-48 family of microporous materials consisting of silicon, aluminium, oxygen and optionally boron. Advantageously in said first embodiment the catalyst (A1) is a crystalline silicate or a dealuminated crystalline silicate.

The crystalline silicate can have a ratio Si/Al of at least about 10.

The crystalline silicate, in an embodiment, can have a ratio Si/Al of at least about 100 and is advantageously selected among the MFI and the MEL.

The crystalline silicate and the dealuminated crystalline silicate are essentially in H-form. It means that a minor part (less than about 50%) can carry metallic compensating ions e.g. Na, Mg, Ca, La, Ni, Ce, Zn, Co.

The dealuminated crystalline silicate is advantageously such as about 10% by weight of the aluminium is removed. Such dealumination is advantageously made by a steaming optionally followed by a leaching.

In another specific embodiment the crystalline silicate catalyst is mixed with a binder, preferably an inorganic binder, and shaped to a desired shape, e.g. pellets. The binder is selected so as to be resistant to the temperature and other conditions employed in the dehydration process of the invention. The binder is an inorganic material selected from clays, silica, metal silicate, metal oxides (such as $ZrO_2$) or gels including mixtures of silica and metal oxides.

According to an embodiment the catalyst is a P-modified zeolite (Phosphorus-modified zeolite). Said phosphorus modified molecular sieves can be prepared based on MFI, MOR, MEL, clinoptilolite or FER, MVVW, TON, EUO, MFS and ZSM-48 family of microporous molecular sieves having an initial Si/Al ratio advantageously between 4 and 500. The P-modified zeolites of this recipe can be obtained based on cheap crystalline silicates with low Si/Al ratio (below 30).

By way of example said P-modified zeolite is made by a process comprising in that order:

selecting a zeolite (advantageously with Si/Al ratio between 4 and 500) among $H^+$ or $NH_4^+$-form of MFI, MEL, FER, MOR, clinoptilolite, MWW, TON, EUO, MFS and ZSM-48;

introducing P at conditions effective to introduce advantageously at least 0.05 wt % of P;

separation of the solid from the liquid if any;

an optional washing step or an optional drying step or an optional drying step followed by a washing step;

a calcination step.

The zeolite with low Si/Al ratio has been made previously with or without direct addition of an organic template.

Optionally the process to make said P-modified zeolite comprises the steps of steaming and leaching. The method consists in steaming followed by leaching. It is generally known by the persons in the art that steam treatment of zeolites, results in aluminium that leaves the zeolite framework and resides as aluminiumoxides in and outside the pores of the zeolite. This transformation is known as dealumination of zeolites and this term will be used throughout the text. The treatment of the steamed zeolite with an acid solution results in dissolution of the extra-framework aluminiumoxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated.

P can be introduced by any means or, by way of example, according to the recipe described in U.S. Pat. Nos. 3,911,041, 5,573,990, WO2009016153, WO 2011089262, WO2013017496, WO2013017497, WO2013017498, and U.S. Pat. No. 6,797,851.

The catalyst made of a P-modified zeolite can be the P-modified zeolite itself or it can be the P-modified zeolite formulated into a catalyst by combining with other materials that provide additional hardness or catalytic activity to the finished catalyst product. Advantageously, at least a part of phosphorous is introduced into zeolite before shaping. In a specific embodiment, the formed P-precursor can be further modified with the metals selected from Mg, Ca, La, Ni, Ce, Zn, Co, Ag, Fe, Cu according to the recipe described in WO 09092779 and WO 09092781.

The separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C., advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering.

Final equilibration step is performed advantageously at the temperature 400-800° C. either in a static condition or in a gas flow. Air, nitrogen or any inert gases can be used.

According to a specific embodiment the phosphorous modified zeolite is made by a process comprising in that order:

selecting a zeolite (advantageously with Si/Al ratio between 4 and 500, from 4 to 30 in a specific embodiment) among $H^+$ or $NH_4^+$-form of MFI, MEL, FER, MOR, clinoptilolite, MWW, TON, EUO, MFS and ZSM-48;

steaming at a temperature ranging from 400 to 870° C. for 0.01-200 h;

leaching with an aqueous acid solution at conditions effective to remove a substantial part of Al from the zeolite;

introducing P with an aqueous solution containing the source of P at conditions effective to introduce advantageously at least 0.05 wt % of P;

separation of the solid from the liquid;

an optional washing step or an optional drying step or an optional drying step followed by a washing step;

a calcination step.

Optionally between the steaming step and the leaching step there is an intermediate step such as, by way of example, contact with silica powder and drying.

Optionally the leaching and introducing P are made simultaneously by using an acid based comprising phosphorus to make the leaching.

Advantageously the selected MFI, MEL, FER, MOR, clinoptilolite, MVVW, TON, EUO, MFS and ZSM-48 (or $H^+$ or $NH_4^+$-form MFI, MEL, FER, MOR, clinoptilolite, MVVW, TON, EUO, MFS and ZSM-48) has an initial atomic ratio Si/Al of 100 or lower and from 4 to 30 in a specific embodiment. The conversion to the $H^+$ or $NH_4^+$-form is known per se and is described in U.S. Pat. Nos. 3,911,041 and 5,573,990.

Advantageously the final P-content is at least 0.05 wt % and preferably between 0.3 and 7 w %. Advantageously at least 10% of Al, in respect to parent zeolite MFI, MEL, FER, MOR and clinoptilolite, MVVW, TON, EUO, MFS and ZSM-48, have been extracted and removed from the zeolite by the leaching.

Then the zeolite either is separated from the washing solution or is dried without separation from the washing solution. Said separation is advantageously made by filtration. Then the zeolite is calcined, by way of example, at 400° C. for 2-10 hours.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen. The steam treatment is preferably carried out for a period of from 0.01 to 200 hours, advantageously from 0.05 to 200 hours, more preferably from 0.05 to 50 hours. The steam treatment tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

The residual P-content is adjusted by P-concentration in the aqueous acid solution containing the source of P, drying conditions and a washing procedure if any. A drying step can be envisaged between filtering and washing steps.

Said P-modified zeolite can be used as itself as a catalyst. In another embodiment it can be formulated into a catalyst by combining with other materials that provide additional hardness or catalytic activity to the finished catalyst product. Materials which can be blended with the P-modified zeolite can be various inert or catalytically active materials, or various binder materials. These materials include compositions such as kaolin and other clays, various forms of rare earth metals, phosphates, alumina or alumina sol, titania, zirconia, quartz, silica or silica sol, and mixtures thereof. These components are effective in densifying the catalyst and increasing the strength of the formulated catalyst. The catalyst may be formulated into pellets, spheres, extruded into other shapes, or formed into a spray-dried particles. The amount of P-modified zeolite which is contained in the final catalyst product ranges from 10 to 90 weight percent of the total catalyst, preferably 20 to 70 weight percent of the total catalyst.

A dehydration catalyst has already been described in WO2009098262.

According to an embodiment the catalyst is a modified crystalline aluminosilicate of the Framework Type FER having Si/Al framework molar ratio greater than 20 and a ratio between strong acid sites and weak acid sites, S/W, lower than 1.0. The ratio S/W is measured by temperature-programmed desorption of ammonia and is determined by the ratio of the peak area of desorbed ammonia above 340° C. to the peak area of desorbed ammonia below 340° C.

In a preferred embodiment, the Framework Type FER is a crystalline aluminosilicate containing advantageously at least one 10 members ring into the structure based on T-atoms, i.e. on the Al and Si atoms contained in said ring. The family of Framework Type FER includes Ferrierite.

In a preferred embodiment, the modified crystalline aluminosilicate of the Framework Type FER is selected from Ferrierite, FU-9, Nu-23, ISI-6, ZSM-35 and SUZ-4. Preferably, the modified crystalline aluminosilicate of the Framework Type FER is Ferrierite.

As mentioned above, the Si/Al framework molar ratio of the modified crystalline aluminosilicate may be greater than 20, preferably, the Si/Al framework molar ratio of the modified crystalline aluminosilicate may be at most 150. Advantageously the modified crystalline aluminosilicate shows a high crystallinity of its zeolite phase, said crystallinity being similar to the crystallinity of the parent zeolite before modification. A similar crystallinity is evidenced via the X ray diffraction patterns (less than 20% of difference measured on the area below the X ray curves).

In a preferred embodiment, the ratio of strong acid sites to weak acid sites, S/W, in said modified crystalline aluminosilicate may be greater than 0.1.

In a preferred embodiment, said modified crystalline aluminosilicate has content in redox metals or cations thereof lower than 1000 ppm, said metals belonging to one of columns 3 to 12 of the Periodic Table. Preferably, said metals are Fe, Co, Ni, Cu, Mo, Mn, Ti, Zn, V, Cr, Ru, Rh, Cd, Pt, Pd, Au, Zr.

In another specific embodiment, the catalyst is mixed with a binder, preferably an inorganic binder. The binder is selected so as to be resistant to the temperature and other conditions employed in the dehydration process of the invention. The binder is an inorganic material selected from clays, silica, metal silicate, metal oxides (such as $ZrO_2$), alumina, aluminophosphate binders, in particular, stoichiometric amorphous aluminophosphate or gels including mixtures of silica and metal oxides.

The modified crystalline aluminosilicate may be in H-form. The H-form of a modified crystalline aluminosilicate of the Framework Type FER means that it comprises oxygen atoms bonded to one aluminium atom and one silicon atom, and which is protonated with a hydrogen atom, resulting in the following sequence —[—Al—O(H)—Si—]—. In the present invention, the modified crystalline aluminosilicate may be essentially under H-form, which means containing less than 1000 ppm of the total amount of the alkali ions and the alkaline earth ions. In another embodiment, the modified crystalline aluminosilicate is partly under H-form. It means that in said modified crystalline aluminosilicate part of the hydrogen atoms bonded to oxygen atoms in the following sequence —[—Al—O(H)—Si—]— is substituted by metallic ions, preferably alkali ions, alkaline earth ions or silver ions. In a preferred embodiment, the modified crystalline aluminosilicate comprises the sequences —[—Al—O(H)—Si—]— and —[—Al—O(X)—Si—]— wherein X is alkali ions, alkaline earth ions or silver ions, the sequence —[—Al—O(X)—Si—]— representing less than 75% based on the total amount of sequences —[—Al—O(H)—Si—]— and —[—Al—O(X)—Si—]— in said modified crystalline aluminosilicate, preferably the sequence —[—Al—O(X)—Si—]— represents less than 50%. Preferably, the alkali ions or alkaline earth ions may be Na, K, Cs, Li, Mg or Ca.

Alternatively, the modified crystalline aluminosilicate may have content in one of the elements selected from the group consisting of lithium, sodium, cesium, magnesium, calcium, potassium and silver, independently from one another, ranging from 10 to 10000 ppm.

According to a specific embodiment the modified crystalline aluminosilicate of the Framework Type FER is made by a process comprising the steps of:
1) providing a crystalline aluminosilicate of the Framework Type FER having Si/Al framework molar ratio greater than or equal to 20, and
2) treating said crystalline aluminosilicate to form a modified crystalline aluminosilicate of the Framework Type FER wherein the Si/Al framework molar ratio is greater than 20 (from 20 to 150 in a specific embodiment), and wherein the ratio of strong acid sites to weak acid sites S/W is lower than 1.0 (greater than 0.1 in a specific embodiment),
3) optionally drying said modified crystalline aluminosilicate formed in step (B) at temperature ranging from 50° C. to 200° C. for a period ranging from 30 min to 24 h, preferably from 1 h to 15 h,
4) optionally, subsequently to the drying step (C), calcining said modified crystalline aluminosilicate formed in step (B) at temperature ranging from 200° C. to 920° C. for a period ranging from 1 h to 48 h.

In a preferred embodiment, the crystalline aluminosilicate of the group Framework Type FER provided in step (1) is selected from Ferrierite, FU-9, Nu-23, ISI-6, ZSM-35 and SUZ-4. Preferably, the crystalline aluminosilicate of the Framework Type FER is Ferrierite. Preferably, the crystalline aluminosilicate provided in step (1) has a ratio of strong acid sites to weak acid sites greater than or equal to 1.0

Preferably, the treatment of step (2) allowing the formation of the modified crystalline aluminosilicate of the Framework Type FER may comprise one or more of the following steps:
(i) treating said crystalline aluminosilicate of the Framework Type FER with an acidic medium, or
(ii) applying partial ion exchange to said crystalline aluminosilicate of the
Framework Type FER, or
(iii) selectively poisoning strong acid sites of the crystalline aluminosilicate of the Framework Type FER by adding a solution comprising alkali salts or alkaline earth salts.

Any of the treatment steps (i) to (iii) may be repeated until the modified crystalline aluminosilicate so-formed reaches the required values with respect to the Si/Al framework molar ratio and with respect to the ratio of strong to weak acid sites. Two or more of the treatment steps (i) to (iii) may be combined together to form the modified crystalline aluminosilicate as defined herein. For example, step (i) or (iii) may be subsequently combined with step (ii) to enhance the properties of the modified crystalline aluminosilicate, in particular of the modified crystalline ferrierite, and of the catalyst composition comprising the same in terms of selectivity, activity or regenerability.

Step (i) of treatment of said crystalline aluminosilicate of the Framework Type FER in an acidic medium may comprise the step of contacting said crystalline aluminosilicate of the Framework Type FER, provided in step (1), with a solution, preferably an aqueous solution, containing one or more organic compounds, each organic compound comprising one or more —$CO_2H$, —$SO_3H$ or —$SO_4H$ groups or salts thereof, preferably two or more —$CO_2H$, —$SO_3H$ or —$SO_4H$ groups or salts thereof. These organic compounds may for example be selected from the group consisting of citric acid, maleic acid, ethylenediaminetetracetic acid, tartaric acid, fumaric acid, oxalic acid, malonic acid, succinic acid, adipic acid, glutaric acid or itaconic acid, phtalic acid, isophtalic acid, nitrilotriacetic acid, hydroxyethylenediaminetriacetic acid, or salts thereof or mixture thereof. The concentration in each one or more organic compounds in said solution may range from $1.10^{-4}$ M to 10 M, preferably from $1.10^{-3}$ M to 1 M. Step (i) may be carried out at temperature ranging from 10° C. to 110° C., preferably from 20° C. to 80° C., preferably from 30 min to 24 h, more preferably from 1 h to 12 h.

Preferably, in said solution, said one or more organic compounds may be under the form of water soluble salt, preferably sodium, potassium, magnesium, calcium, lithium, cesium or silver salt or mixture thereof. When a salt of said one or more organic compounds is used, the amount and the concentration of the solution comprising the same can be adjusted such that, in the so-formed modified crystalline aluminosilicate, the sequence —[—Al—O(X)—Si—]— wherein X is alkali, alkaline earth or silver ions, represents at most 75% of the total amount of sequences —[—Al—O(X)—Si—]— and —[—Al—O(H)—Si—]—, preferably at most 50%, more preferably at most 25%, and preferably at least 1%, more preferably at least 5%, most preferably at least 10%.

The step (ii) of applying ion exchange to the crystalline aluminosilicate to form the modified crystalline aluminosilicate may be carried out by contacting said crystalline aluminosilicate with a solution containing one or more inorganic salts such as inorganic ammonium salt, inorganic calcium salt, inorganic lithium salt, inorganic sodium salt, inorganic potassium salt, inorganic magnesium salt or inorganic silver salt. Inorganic salt may be salt of nitric acid, halogenic acid, sulfuric acid, sulfurous acid, nitrous acid or mixture thereof, preferably nitric acid or halogenic acid or mixture thereof. The concentration of each inorganic salt in said solution may range from $1.10^{-4}$ M to 10 M, preferably from $1.10^{-3}$ M to 1 M. Step (ii) may be carried out at temperature ranging from 10° C. to 110° C., preferably from 20° C. to 80° C., preferably for 30 min to 24 h, more preferably for 1 h to 10 h. Preferably, the solution may contain ammonium salt, calcium salt or lithium salt of nitric acid or halogenic acid.

The step (iii) of selectively poisoning strong acid sites of the crystalline aluminosilicate to form the modified crystalline aluminosilicate may be carried out by impregnating said crystalline aluminosilicate of step (1) with an aqueous solution containing alkali ions or alkaline earth ions, preferably sodium, lithium, potassium, cesium, magnesium or calcium ions or mixture thereof. The amount and the concentration of said aqueous solution containing alkali ions or alkaline earth ions can be adjusted such that in the so-formed modified crystalline aluminosilicate, the sequence —[—Al—O(X)—Si—]— wherein X is alkali ions or alkaline earth ions, as defined above, represents at most 75% of the total amount of sequences —[—Al—O(X)—Si—]— and —[—Al—O(X)—Si—]—, preferably at most 50%, more preferably at most 25%, and preferably at least 1%, more preferably at least 5%, most preferably at least 10%. In particular, the concentration of said solution ranges from $1.10^{-4}$ M to 10 M, preferably from $1.10^{-3}$ M to 5 M. Step (iii) may be carried out at temperature ranging from 10° C. to 100° C., preferably from 20° C. to 30° C. The suspension or solution formed by contacting said crystalline aluminosilicate of step (1) with an aqueous solution containing alkali ions or alkaline earth ions may be further heated at temperature ranging from 50° C. to 100° C., for a period ranging from 1 h to 24 h.

Prior or subsequently to step (2) of the present process, the modified crystalline aluminosilicate or the crystalline aluminosilicate may be mixed with a binder, preferably an inorganic binder. Typically, the binder and the crystalline aluminosilicate, modified or not, are mixed together by a mixing process. In such a process, the binder, for example silica, in the form of a gel is mixed with the crystalline aluminosilicate, modified or not. The resultant mixture is extruded into the desired shape, for example cylindrical or multi-lobe bars. Spherical shapes can be made in rotating granulators or by oil-drop technique. Small spheres can further be made by spray-drying a catalyst-binder suspension. Thereafter, the extruded material containing the binder and the crystalline aluminosilicate, modified or not, is calcined in air or an inert gas, typically at a temperature of from 200 to 900° C. for a period of from 1 to 48 hours. Preferably, said binder is selected from the group consisting of clays, alumina, silica-alumina, silica, titania, aluminophosphate, titania-silica. Hence, according to the present process, the crystalline aluminosilicate provided in step (1) may encompass the extruded material containing the binder and the crystalline aluminosilicate as described herein.

According to another specific embodiment, suitable catalysts for the present process are silicoaluminophosphate molecular sieves, in particular of the AEL group with typical example the SAPO-11 molecular sieve. The SAPO-11 molecular sieve is based on the ALPO-11, having essentially an Al/P ratio of 1 atom/atom. During the synthesis silicon precursor is added and insertion of silicon in the ALPO framework results in an acid site at the surface of the micropores of the 10-membered ring sieve. The silicon content ranges from 0.1 to 10 atom % (Al+P+Si is 100).

According to another specific embodiment, another family of suitable catalysts for the dehydration are alumina's as such, silica-alumina's or alumina's that have been modified by surface treatment with silicon, zirconium, titanium or fluor. Alumina's are generally characterized by a rather broad acid strength distribution and having both Lewis-type and Bronsted-type acid sites. The presence of a broad acid strength distribution makes the catalysis of several reactions, requiring each a different acid strength, possible. This often results in low selectivity for the desired product. Deposition of silicon, zirconium, titanium or fluor on the surface of alumina allows rendering the catalyst significantly more selective. For the preparation of the alumina based catalyst, suitable commercial alumina's can be used, preferably eta or gamma alumina, having a surface area of 10 to 500 m²/gram and an alkali content of less than 0.5%. The catalyst according to the present invention is prepared by adding 0.05 to 10% of silicon, zirconium or titanium. The addition of these metals can be done during the preparation of the alumina or can be added to the existing alumina, eventually already activated. Addition of the metal during the preparation of the alumina can be done by dissolving the metal precursor together with the aluminium precursor before precipitation of the final alumina or by addition of the metal precursor to the aluminium hydroxide gel. A preferred method is adding metal precursors to the shaped alumina. Metal precursors are dissolved in a suitable solvent, either aqueous or organic, and contacted with the alumina by incipient wetness impregnation or by wet impregnation or by contacting with an excess of solute during a given time, followed by removing the excess solute. The alumina can also be contacted with vapour of the metal precursor. Suitable metal precursors are halides of silicon, zirconium or titanium, oxyhalides of zirconium or titanium; alcoxides of silicon, zirconium or titanium; oxalates or citrates of zirconium or titanium or mixtures of the above. The solvent is selected according to the solubility of the metal precursor. The contacting can be done at temperature of 0° C. to 500° C., most preferred from 10° C. to 200° C. After the contacting, the alumina is eventually washed, dried and finally calcined in other to enhance the surface reaction between the silicon, zirconium or titanium and the alumina and the removal of the metal precursor ligands. The use of silicated, zirconated or titanated or fluorinated alumina's for the dehydration is preferably done in the presence of water. The weight ratio of water to alcohol ranges from 1/25 to 3/1. Fluorinated alumina is known in itself and can be made according to the prior art.

According to an embodiment the catalyst is any of above cited catalyst which is subjected to a preliminary in-situ or ex-situ pre-coking step before use. The pre-coking step may be performed in presence of the alcohol to dehydrate, preferably in presence of iso-butanol. In a first embodiment, the pre-coking may be performed at a temperature from 300° C. to 450° C., advantageously from 400° C. to 450° C., under a pressure from 0.1 to 0.5 MPa and a WHSV from 0.1 to 3 h$^{-1}$. In another embodiment, the pre-coking step may be performed at a temperature from 250 to 450° C., preferably from 300 to 350° C., a pressure from 1.1 to 3 MPa, preferably from 1.2 and 3 MPa and a WHSV from 0.1 and 3 h$^{-1}$. In both embodiments, pre-coking may be performed during 2 to 30 hours, preferably from 6 to 24 hours. Advantageously, the precooking is either performed at a temperature higher than the dehydration temperature or at a pressure higher than the dehydration pressure.

As regards the addition of sulfur containing compound(s), one or more sulfur containing compound may be added to feed (A) or directly in the dehydration unit such that the undesired by-products in the effluent (B) are reduced by comparison with a non introduction of sulfur containing compound. Undesired by-products are aldehyde(s), in particular aldehyde(s) corresponding to the alcohol(s) to dehydrate, as well as $H_2$, CO, $CO_2$ and $CH_4$.

Sulfur containing compound may also mean a precursor of a sulfur containing compound.

The man skilled in the art can easily determine, by following the by-products in the effluent and the percentage of said by-products whether a sulfur containing compound is appropriate.

Various sulfur containing compounds, in particular organosulfur compounds, can be used. Advantageously, degradable organosulfur compounds can be used, in other words organosulfur compounds than may partially decompose to $H_2S$ under the conditions of dehydration.

Organosulfur compounds that can be used are thiols, sulfides and disulfides, as for example:
  thiols of general formula R—SH, where R represents an alkane, alkene, or other carbon-containing group of atoms,
  sulfides of general formula R—S—R', where R and R', identical or different, represent an alkane, alkene, or other carbon-containing group of atoms,
  disulfides of general formula R—S—S—R', where R and R', identical or different, represent an alkane, alkene, or other carbon-containing group of atoms Among thiols, sulfides and disulfides, those where R and/or R' present a carbon chain of 1 to 10 carbon atoms are preferred, such as for example dimethyldisulfide (DMDS).

Amounts of sulphur containing compound (in sulfur element) can range from 0.1 to 100 wppm, advantageously from 0.1 to 50 wppm, preferably from 0.2 to 25 wppm, more preferably from 0.5 to 10 wppm, relative to the alcohol.

The sulfur containing compound can be introduced in the dehydration unit by (i) blending with the alcohol feedstock, (ii) blending with a part of the alcohol feedstock which is subsequently introduced in the dehydration unit with the remaining alcohol feedstock, (iii) blended with the inert diluent which is subsequently introduced in the dehydration unit with the alcohol feedstock, (iv) blended with water which is subsequently introduced in the dehydration unit with the alcohol feedstock or (v) blended with one of the streams that is recycled back to the dehydration unit, like non-converted alcohol, water or inert diluents or (vi) blending an alcohol feedstock being substantially free from sulfur containing compound with an alcohol feedstock containing already <0.5 wppm sulfur containing compound. In the latter case the sulfur containing compound is originating from the production process where the alcohol feedstock was produced as for instance the fermentation process of carbohydrates into alcohol where trace amounts of sulfur containing compound are inherently part of the production process and are left in the final alcohol product.

In an embodiment, only alcohol feedstock containing already sulfur containing compound in appropriate quantities is used.

As regards to the metallic sites contained in the dehydration unit, they can either originate from the reactor walls or from the acidic catalyst itself as impurities. It has been particularly discovered that the metallic reactor walls can be activated during the alcohol dehydration reaction and under the alcohol dehydration reaction. It is also possible that the acidic catalyst contains metallic impurities originated from its method of preparation. Metallic impurities can also originate from rust being deposited on the acidic catalyst during the loading or during the operation. Said rust being then activated during the dehydration reaction.

EXAMPLES

The ethanol conversion is the ratio (ethanol introduced in the reactor—ethanol leaving the reactor)/(ethanol introduced in the reactor).

The ethylene yield is the ratio, on carbon basis, (ethylene leaving the reactor)/(ethanol introduced in the reactor).

The ethylene selectivity is the ratio, on carbon basis, (ethylene leaving the reactor)/(ethanol converted in the reactor).

Experimental:

Tests were performed on 200 ml of catalyst grains in form of extrudates homegeneously blended with 200 ml of SiC 1.6 mm.

Two tubular adiabatic reactors with internal diameter 38 mm were loaded with a blend of 200 ml of catalyst, which were blended with 200 ml of SiC (100 ml of catalyst per reactor). The reactors were installed in a series with an intermediate reheating. The temperature profile is monitored with the aid of a thermowell placed inside the reactors. The reactor temperature is increased at a rate of 60° C./h to 550° C. under nitrogen, kept 1 hour at 550° C. and then cooled down to the initial reaction temperature under nitrogen. The nitrogen is then replaced by the feed at the indicated operating conditions.

Analysis of the products is performed by using on-line chromatography:
- a gas chromatography with a FID (flame ionization detector), for measuring ethylene, acetaldehyde and other hydrocarbons,
- a gas chromatography with a TCD (thermal conductivity detector) for measuring CO, $CO_2$, $H_2$ and $CH_4$.

The total amount of sulfur (present in the form of organosulfur compound(s) in ethanol) is determined by Ultra Violet Fluorescence, using, for example Antek 9000 apparatus. The detail analysis of the nature of sulphur compounds, which are present in the alcohol, is performed via a gas chromatography with a SCD detector (Sulfur Chem iluminescence Detector).

Determination of the amount of sulfur (originating from organosulfur compounds) relative to the ethanol is performed using a calibration in ethanol with a calibration using thiophenone, or using the norm NF EN 15486.

bio-ethanol (Ethanol Surfin & Copersugar)

The characteristics of the bio-ethanol used in the examples below are gathered table 1.

TABLE 1

Main characteristics of bio-ethanol

| | | Ethanol Surfin (food industry) | Raw bio-ethanol from Copersucar S.A. |
|---|---|---|---|
| Density @15° C. | g/ml | 0.8100 | 0.8144 |
| EtOH content | wt % | 94.5 | 92.9 |
| Sulfur | ppm | <0.5 | 2.7 |
| Other impurities | | | |
| Aldehydes | ppm | 7 | 182 |
| Esters | ppm | 0 | 74 |
| Higher alcohols | ppm | 10 | 413 |
| Acids | ppm | <1 | <1 |

Catalyst:

The catalyst is a phosphorous modified zeolite (P-ZSMS), prepared according to the following recipe. A sample of zeolite ZSM-5 (Si/Al=12) in $NH_4$-form (containing 250 ppm of Na and synthesized without template) was blended with a silica binder in a weight ratio 80:20 followed by addition of extrusion additives and shaping. A final Na content in the catalyst was 320 wppm.

The extruded sample was dried for 2 h at 140° C., calcined for 2 h at 600° C. followed by steaming at 550° C. for 6 h in 100% steam.

Steamed solid was incipient wetness impregnated with an aqueous solution of phosphoric acid to introduce about 3 wt % of phosphorus to the catalyst. The impregnated solid was dried for 16 h at 110° C.

Then, the phosphated sample was incipient wetness impregnated with a solution of calcium nitrate obtained by dissolution of calcium carbonate to introduce about 1 wt % of calcium to the solid. The impregnated solid was dried for 16 h at 110° C. Resulted catalyst containing 2.8 wt % of phosphorus and 0.8% of calcium was steamed at 750° C. for 1 h in 100% of steam.

Comparative Example

In this example, a mixture of 25% wt Surfin bio-ethanol containing less than 0.5 wppm of sulfur and 75% wt water has been processed on the catalyst under the following dehydration conditions: outlet pressure of 4 barg, a weight hour space velocity (WHSV) referred to Surfin bio-ethanol of 7 $h^{-1}$, downflow. At the start of the run (time of stream of 7 h), inlet temperature of the first reactor is of 400° C. and inlet temperature of the second reactor is of 425° C. After several hours of run, the inlet temperature of the first reactor is increased to 410° C. and the inlet temperature of the second reactor is increased to 430° C. Such increase of inlet temperatures permits to compensate for the lost of activity of the catalyst as a function of time on stream.

Table 2 gives the results of the ethanol conversion and the ethylene yield at the start of run and for a time of stream of more than 100 hours. Table 2 shows that under the defined operating conditions, formation of acetaldehyde, CO and $H_2$ is observed, even after a long time of stream, with a decrease of yield of ethylene and selectivity to ethylene. The values are given in weight percent on carbon basis, coke free basis.

TABLE 2

Results of the dehydration in absence of sulfur containing compound using Surfin bio-ethanol diluted with 75% wt water, at the start of the run and after more than 100 hours of run.

| FEED | ETOH (Surfin)/$H_2O$ 25/75 wt % | ETOH (Surfin)/$H_2O$ 25/75 wt % |
|---|---|---|
| S-content Wppm in alcohol | <0.5 | <0.5 |
| Time-on-stream (h) | 24-50 | >100 |
| WHSV ($h^{-1}$) | 7 | 7 |
| P (barg) | 4 | 4 |
| $T_{inlet}$ (° C.) Reactor 1 | 400 | 410 |
| $T_{inlet}$ (° C.) Reactor 2 | 425 | 430 |
| Conversion (% wt CH2) | 99.4 | 99.6 |
| Analysis of by-products | | |
| Yield of ethylene, wt % | 97.2 | 96.7 |
| Selectivity to ethylene, % | 97.8 | 97.1 |
| Acetaldéhyde, wt % | 1.37 | 0.60 |
| $H_2$, mol % | 1.67 | 0.79 |
| $CH_4$, vppm | 53 | 33 |

TABLE 2-continued

Results of the dehydration in absence of sulfur containing compound using Surfin bio-ethanol diluted with 75% wt water, at the start of the run and after more than 100 hours of run.

| FEED | ETOH (Surfin)/$H_2O$ 25/75 wt % | ETOH (Surfin)/$H_2O$ 25/75 wt % |
|---|---|---|
| CO, vppm | 135 | 43 |
| $CO_2$, vppm | 200 | 129 |

Example 1 (According to the Invention)

In this example, a mixture of 25% wt of bio-ethanol (Surfin) and 75% wt water, containing 2 wppm of sulfur as DMDS (doped with 2 ppm of S as DMDS), has been processed on the catalyst under the following dehydration conditions:outlet pressure of 4 barg, a weight hour space velocity referred to raw ethanol of 7 $h^{-1}$, downflow. Inlet temperature of the first reactor is of 410° C. and inlet temperature of the second reactor is of 430° C. These conditions are maintained during all the test.

Table 3 gives the results of the ethanol conversion and the ethylene yield at the start of run (time of stream from 24 to 50 hours) and for a time of stream of more than 100 hours. The use of a controlled amount of sulfur containing compound (in this case DMDS) allows reducing formation of acetaldehyde, CO and $H_2$ without jeopardizing the time on stream performance. Such reduction is observed at the start of the run and continues after a long time of stream, contrarily to a feed without sulfur containing compound as in the comparative example. Yield of ethylene as well as selectivity to ethylene also increases during the test.

TABLE 3

Results of the dehydration in presence of sulfur containing compound using Surfin bio-ethanol diluted with 75% wt water at the start of the run and after more than 100 hours of run

| FEED | ETOH (Surfin)/$H_2O$ 25/75 wt % | ETOH (Surfin)/$H_2O$ 25/75 wt % |
|---|---|---|
| S-content Wppm in alcohol | 2 (doped with DMDS) | 2 (doped with DMDS) |
| Time-on-stream (h) | 24-50 | >100 |
| WHSV ($h^{-1}$) | 7 | 7 |
| P (barg) | 4 | 4 |
| $T_{inlet}$ (° C.) Reactor 1 | 410 | 410 |
| $T_{inlet}$ (° C.) Reactor 2 | 430 | 430 |
| Conversion (% wt CH2) | 99.7 | 99.7 |
| Analysis of by-products | | |
| Yield of ethylene, wt % | 97.9 | 98.2 |
| Selectivity to ethylene, % | 98.2 | 98.5 |
| Acetaldéhyde, wt % | 0.55 | 0.57 |
| $H_2$, mol % | 0.69 | 0.56 |
| $CH_4$, vppm | 18 | 31 |
| CO, vppm | 36 | 22 |
| $CO_2$, vppm | 123 | 112 |

Example 2 (According to the Invention)

In this example, a mixture of 25% wt of bio-ethanol (Surfin) and 75% wt water, containing 4 wppm of sulfur as DMDS, has been processed on the catalyst under the following dehydration conditions:outlet pressure of 4 barg, a weight hour space velocity referred to raw ethanol of 7 $h^{-1}$, downflow. The inlet temperature of the first reactor is of 410° C. and the inlet temperature of the second reactor is of 429° C.

Table 4 gives the results of the ethanol conversion and the ethylene yield for a time of stream of more than 100 hours. The use of an increased amount of sulfur containing compound with respect to example 1 still permits to reduce formation of acetaldehyde, CO and $H_2$ without jeopardizing the time on stream performance, even after a long time of stream.

TABLE 4

Results of the dehydration in presence of sulfur containing compound using Surfin bio-ethanol diluted with 75% wt water after more than 100 hours of run

| FEED | ETOH (Surfin)/$H_2O$ 25/75 wt % |
|---|---|
| S-content Wppm in alcohol | 4 (doped with DMDS) |
| Time-on-stream (h) | >100 |
| WHSV ($h^{-1}$) | 7 |
| P (barg) | 4 |
| $T_{inlet}$ (° C.) Reactor 1 | 410 |
| $T_{inlet}$ (° C.) Reactor 2 | 429 |
| Conversion (% wt CH2) | 98.5 |
| Analysis of by-products | |
| Yield of ethylene, wt % | 98.2 |
| Selectivity to ethylene, % | 99.7 |
| Acetaldéhyde, wt % | 0.48 |
| $H_2$, mol % | 0.48 |
| $CH_4$, vppm | 29 |
| CO, vppm | 21 |
| $CO_2$, vppm | 96 |

Example 4 (According to the Invention)

In this example, a mixture of 25% wt of raw ethanol from Copersucar, containing with 2.7 wppm of sulfur, and 75% wt water has been processed on the catalyst under the following dehydration conditions:outlet pressure of 4 barg, a weight hour space velocity referred to raw ethanol of 7 $h^{-1}$, inlet temperature of 410° C. in the first reactor and inlet temperature of 430° C. in the second reactor, downflow.

Table 5 gives the results of the ethanol conversion and the ethylene yield for a time of stream of more than 100 hours. Improved results are observed in comparison with an ethanol stream without sulfur as the one processed in the comparative example.

TABLE 5

Results of the dehydration using raw bio-ethanol from Copersucar containing 2.7 ppm of S diluted with 75% wt water after more than 100 hours of run.

| FEED | Raw bio-ethanol (Copersucar)/$H_2O$ 25/75 wt % |
|---|---|
| S-content Wppm in alcohol | 2.7 |
| Time-on-stream (h) | >100 |
| WHSV ($h^{-1}$) | 7 |
| P (barg) | 4 |
| $T_{inlet}$ (° C.) Reactor 1 | 410 |
| $T_{inlet}$ (° C.) Reactor 2 | 430 |
| Conversion (% wt CH2) | 98.9 |
| Analysis of by-products | |
| Yield of ethylene, wt % | 97.8 |
| Selectivity to ethylene, % | 98.9 |
| Acetaldéhyde, wt % | 0.52 |
| $H_2$, mol % | 0.50 |

TABLE 5-continued

Results of the dehydration using raw bio-ethanol from Copersucar containing 2.7 ppm of S diluted with 75% wt water after more than 100 hours of run.

| FEED | Raw bio-ethanol (Copersucar)/H$_2$O 25/75 wt % |
|---|---|
| CH$_4$, vppm | 27 |
| CO, vppm | 22 |
| CO$_2$, vppm | 116 |

The invention claimed is:

1. A process for dehydrating an alcohol to prepare one or more corresponding olefins, the process comprising:
   (a) forming an acidic catalyst selected from modified crystalline aluminosilicates of the Framework Type FER having Si/Al framework molar ratio greater than 20 and a ratio between strong acid sites and weak acid sites, S/W, lower than 1.0, the ratio S/W being measured by temperature-programmed desorption of ammonia and being determined by the ratio of the peak area of ammonia desorbed above 340° C. to that desorbed below 340° by:
      (1) providing a crystalline aluminosilicate of the Framework Type FER having an Si/Al framework molar ratio of greater than or equal to 20, and
      (2) treating said crystalline aluminosilicate of (1) to form the modified crystalline aluminosilicate of the Framework Type FER having the Si/Al framework molar ratio greater than 20 and the ratio between strong acid sites and weak acid sites, S/W, lower than 1.0 by at least one treatment step selected from: (i) contacting said crystalline aluminosilicate of the Framework Type FER with a solution containing one or more organic compounds, wherein each of the one or more organic compounds comprises one or more —CO$_2$H, —SO$_3$H, or —SO$_4$H groups or salts thereof, and wherein a concentration of each of the one or more organic compounds in the solution containing the one or more organic compounds is in a range of from 1×10$^{-4}$ Molar (M) to 10 M; (ii) applying partial ion exchange to said crystalline aluminosilicate of the Framework Type FER (iii) selectively poisoning strong acid sites of the crystalline aluminosilicate of the Framework Type FER: or (iv) a combination thereof:
   (b) introducing into a dehydration unit containing metallic sites a feed (A) comprising one or more alcohols having at least 2 carbon atoms, optionally water, and optionally an inert component, and one or more sulfur containing compounds in an amount of from 0.5 wt ppm to 20 wt ppm of the total content of the feed (A),
   (c) contacting the feed (A) with the acidic catalyst in a reaction zone of the dehydration unit at conditions effective to dehydrate at least a portion of the alcohol to make a corresponding olefin or mixture of olefins,
   (d) recovering from the dehydration unit an effluent (B) comprising an olefin or mixture of olefins, water, undesired by-products including aldehydes, H$_2$, CO, CO$_2$, and CH$_4$, optionally one or more unconverted alcohols, and optionally the inert component, and
   (e) determining the amount of the one or more sulfur containing compounds in the feed (A) introduced into the dehydration unit at (b) by: performing (c) with a feed (A) not comprising said one or more sulfur containing compounds, measuring an amount of the undesired by-products in the effluent (B) recovered at (d), and increasing the amount of said one or more sulfur containing compounds until the amount of the undesired by-products in the effluent (B) recovered at (d) is less than 4 wt %.

2. The process according to claim 1, wherein the dehydration unit comprises at least one metallic internal wall.

3. The process according to claim 1, wherein the introducing step (b) comprises adding one or more sulfur-containing compounds to the feed (A) or directly in the dehydration unit.

4. The process according to claim 1, wherein the one or more sulfur-containing compounds is at least one compound selected from the group consisting of thiols, sulfides and disulfides.

5. The process according to claim 1, wherein:
   the recovery step (d) comprises recovering one or more unconverted alcohols, the process further comprising, subsequent to recovery step (d), a step of:
   (f) recycling the unconverted alcohol to the introducing step (b), in the dehydration unit.

6. The process according to claim 1, wherein the recovering step (d) comprises recovering the one or more olefins and the one or more unconverted alcohols, as well as each compound contained in the effluent (B), by fractionation.

7. The process according to claim 1, wherein the one or more alcohols provided in step (b) comprise one or more alcohols derived from edible or non-edible biomass.

8. The process according to claim 1, wherein the one or more alcohols provided in step (b) comprise one or more alcohols obtained via syn-gas route or synthesized via partial oxidation of paraffin.

9. The process according to claim 1, wherein the one or more alcohols provided in step (b) comprise one or more alcohols produced via hydrogenation of corresponding aldehydes, ketones or acids derived from the edible or non-edible biomass.

10. The process according to claim 1, where the one or more olefins recovered in step (d) are used for production of polymers and elastomers.

11. The process according to claim 1, where the one or more olefins recovered in step (d) are used for production of fuel.

12. The process according to claim 1, wherein the dehydration unit is operated at a pressure ranging from 0.5 to 30 bars absolute (50 kPa to 3 MPa).

13. The process according to claim 1, wherein the dehydration unit is operated at a temperature of from 220° C. to at most 500° C.

14. The process of claim 1, further comprising subjecting the acidic catalyst to a preliminary pre-coking step.

15. The process of claim 1, wherein the one or more treatment steps include at least two of treatment steps (i), (ii), or (iii); repetition of at least one of treatment steps (i), (ii), or (iii); or a combination thereof.

16. The process of claim 15, wherein the one or more treatment steps include (i) or (iii) subsequently combined with (ii).

17. The process of claim 1, wherein (ii) comprises contacting said crystalline aluminosilicate of the Framework Type FER with a solution containing one or more inorganic salts, wherein a concentration of the one or more inorganic salts in the solution containing the one or more inorganic salts is in a range of from 1×10$^{-4}$ Molar (M) to 10 M.

18. The process of claim 1, wherein (iii) comprises impregnating said crystalline aluminosilicate of the Framework Type FER with an aqueous solution containing alkali ions, alkaline earth ions, or mixtures thereof.

19. The process of claim 1, wherein the ratio between the strong acid sites and the weak acid sites, S/W, is greater than 0.1.

* * * * *